(12) United States Patent
Schinazi et al.

(10) Patent No.: US 6,911,470 B1
(45) Date of Patent: Jun. 28, 2005

(54) POLYOXOMETALATE COMPOUNDS AS ANTIVIRAL AGENTS

(76) Inventors: Raymond F. Schinazi, 1524 Regency Walk Dr., Decatur, GA (US) 30033; Craig L. Hill, 2941 Cravey Dr., Atlanta, GA (US) 30345

( * ) Notice: Subject to any disclaimer, the term of this patent is extended or adjusted under 35 U.S.C. 154(b) by 0 days.

(21) Appl. No.: 08/140,885

(22) Filed: Oct. 25, 1993

Related U.S. Application Data

(63) Continuation of application No. 08/024,837, filed on Mar. 1, 1993, now abandoned, which is a continuation of application No. 07/474,389, filed on Feb. 5, 1990, now abandoned, which is a continuation-in-part of application No. 07/247,641, filed on Sep. 22, 1988, now abandoned.

(51) Int. Cl.$^7$ .............................................. A61K 31/28
(52) U.S. Cl. ....................... 514/492; 424/604; 424/617; 252/389.54; 423/53; 423/594.13; 423/606; 562/562; 562/560; 548/344
(58) Field of Search ............................. 514/12–19, 492; 424/604, 617; 252/389.54; 423/53, 594.13, 606; 562/562, 560; 548/344

(56) References Cited

U.S. PATENT DOCUMENTS

| | | | | |
|---|---|---|---|---|
| 4,590,298 A | * | 5/1986 | Che ............................ | 568/387 |
| 4,634,502 A | * | 1/1987 | Callahan et al. .............. | 204/23 |
| 4,681,933 A | | 7/1987 | Chu et al. ..................... | 536/23 |
| 4,759,929 A | * | 7/1988 | Chermann et al. .......... | 424/131 |
| 4,839,008 A | * | 6/1989 | Hill ........................ | 204/157.15 |
| 4,841,039 A | | 6/1989 | Chu et al. ..................... | 536/29 |
| 4,864,041 A | * | 9/1989 | Hill ............................. | 549/513 |
| 4,916,122 A | | 4/1990 | Chu et al. ..................... | 514/50 |
| 5,077,279 A | | 12/1991 | Chu et al. ..................... | 519/49 |
| 5,084,445 A | | 1/1992 | Chu et al. ..................... | 514/49 |

OTHER PUBLICATIONS

Ablashi et al, *Europ. J. Genet.*, vol. 13, pp. 713–720, (1977).
Blancou et al, *J. Am. Soc. Microbiol.*, vol. 2, pp. 1070–1071 (1982).
Chermann et al, *Biochemical and Biophysical Research Communications*, vol. 65, pp. 1229–1235 (1975).
Bussereau et al, *Ann. Virol.*, vol. 134E, pp. 487–506 (1983).
Werner et al, *J. gen Virol.*, vol. 31, pp. 59–64 (1976).
Tsiang et al, *J. gen. Virol.*, vol. 40, pp. 665–668 (1978).
Turner et al, *Proc. Soc. Exp. Biol. Med.*, vol. 138, pp. 1030–1034 (1971).
Souyri–Coporate et al, *J. gen.Virol.*, vol 65, pp. 831–835 (1984).
Pepin et al, *Archives of Virology*, vol. 83, pp. 327–329 (1985).
Larnicol et al, *J. gen. Virol.*, vol. 55, pp. 17–23 (1981).
Kimberlin et al, *The Lancet*, Sep. 15, 1979, pp. 591–592.
Kimberlin et al, *Archives of Virology*, vol. 78, pp. 9–18 (1983).

Kimberlin et al, *Antimicrobial Agents and Chemotherapy*, vol. 30, pp. 409–413 (1986).
Jasmin et al, *Biomedicine*, vol. 18, pp. 319–327 (1973).
Jasmin et al, *Journal of the National Cancer Institute*, vol. 53, pp. 469–474 (1974).
Dormont et al, *Cancer Detection and Prevention*, vol. 12, pp. 181–194 (1988).
Alizadeh et al, *J. Am. Chem. Soc.*, vol. 107, pp. 2662–2669 (1985).
Finke et al, *J. Am. Chem. Soc.*, vol. 103, pp. 1587–1589 (1981).
Brevard et al, *J. Am. Chem. Soc.*, vol. 105, pp. 7059–7063 (1983).
Knoth et al, *Inorg. Chem.*, vol. 25, pp. 1577–1584 (1986).
Finke et al, *Inorg. Chem.*, vol. 26, pp. 3886–3896 (1987).
Ikeda et al, *Antiviral Chemistry & Chemotherapy*, vol. 4(5), pp. 253–262 (1993).
Ruprecht et al, *Nature*, vol. 323, pp. 467–469 (1986).
Take et al, *Antiviral Research*, vol. 15, pp. 113–124 (1991).

* cited by examiner

*Primary Examiner*—Jon Weber
*Assistant Examiner*—David Lukton
(74) *Attorney, Agent, or Firm*—King & Spalding LLP; Sherry M. Knowles, Esq.

(57) ABSTRACT

Polyoxometalate compounds which exhibit anti-retroviral activity are disclosed. Compounds with anti-retroviral activity include those having the following general molecular formulas:

$M_7PW_{11}O_{39}$ $M_8SiW_{11}O_{39}$ $M_9HSiW_9O_{34}$ $M_8HPW_9O_{34}$ $M_{10}(TM)_4(PW_9O_{34})_2$ $M_{16}(TM)_4(P_2W_{15}O_{56})_2$ $M_{14}[NaP_5W_{30}O_{110}]$ $M_{12}(TM)_3(PW_9O_{34})_2$ $M_6P_2W_{18}O_{62}$ wherein M is an alkali metal, $NH_4^+$ or other common monocation or soluble dication, or any combination of the above provided adequate water solubility is exhibited, or histidinium ion, argininium ion, or lysinium ion or any dication of a dipeptide or oligopeptide with 2 protonated basic amino acid residues, or any combination of these monocations or dications with each other or with any common inorganic cation, and TM is a divalent transition metal ion, such as Mn, Fe, Co, Ni, Cu and Zn.

20 Claims, 7 Drawing Sheets

POLYOXOMETALATE COMPOUNDS AS ANTIVIRAL AGENTS

This application is a continuation of application Ser. No. 08/024,837 filed Mar. 1, 1993, now abandoned, which is a continuation of application Ser. No. 07/474,389 filed Feb. 5, 1990, now abandoned, which is a continuation-in-part of application Ser. No. 07/247,641 filed Sep. 22, 1988, now abandoned.

BACKGROUND OF THE INVENTION

1. Field of the Invention

The present invention relates to certain polyoxometalate compounds, particularly amino acid salts of polyoxometalate compounds, and their use as antiviral agents. These agents can be advantageously used, for example, in the treatment of infection by retroviruses such as HIV (HTLV-III/LAV), which causes acquired immuno-deficiency syndrome (AIDS).

2. Background Information

AIDS was first recognized as early as 1979. The number of cases reported to the Centers for Disease Control (CDC) increased dramatically each year since then, and in 1982 the CDC declared AIDS a new epidemic. Between December 1987 and November 1988, over 32,000 new cases of AIDS were reported by the CDC (HIV/AIDS Surveillance Report, 1–16, December 1989). Over 3,000 new cases were reported in 1984 alone. The WHO estimates that at least 200,000 cases of the disease have occurred worldwide. It has also been estimated that approximately 5,000,000 people are infected today with HIV and at least 1,000,000 new cases of AIDS may be expected during the next 5 years.

In the United States, about 115,000 cases of AIDS have been reported to the U.S. Centers for Disease Control (CDC) to date. Nearly 28,000 were reported in 1987 alone. It has been predicted that in the United States 365,000 to 380,000 total cases will be reported by 1992. The CDC believes that 1 million to 1.5 million Americans are now infected with HIV. It is clear that the cost of the AIDS epidemic in terms of human lives is staggering, and the worst is yet to come.

Retroviruses were proposed as the causative agent of AIDS. Two such retroviruses now known to cause AIDS have been identified and isolated: LAV (lymphadenopathy-associated virus) and HTLV-III (human T-cell leukemia virus). It was later determined that LAV and HTLV-III are identical. Recently, human immunodeficiency virus type 1 (HIV) has emerged as a preferred name for the virus responsible for AIDS. Antibodies to HIV are present in over 80% of patients diagnosed as having AIDS or pre-AIDS syndrome, and it has also been found with high frequency in identified risk groups.

There is considerable difficulty in diagnosing the risk of development of AIDS. AIDS is known to eventually develop in almost all of the individuals infected with HIV.

A patient is generally diagnosed as having AIDS when a previously healthy adult with an intact immune system acquires impaired T-cell immunity. The impaired immunity usually appears over a period of 18 months to 3 years. As a result of this impaired immunity, the patient becomes susceptible to opportunistic infections, various types of cancers such as Kaposi's sarcoma, and other disorders associated with reduced functioning of the immune system.

Another condition associated with HIV is AIDS-related complex, or ARC. This condition can lead to AIDS in some cases.

No treatment capable of preventing the disease or significantly reversing the immunodeficiency of AIDS or ARC is currently available. All patients with opportunistic infections and approximately half of all patients with Kaposi's sarcoma have died within two years of diagnosis. Attempts at reviving the immune systems in patients with AIDS have been unsuccessful.

It has been reported that 3'-azido-3'-deoxythymidine (AZT) is an antiviral agent that inhibits the infectivity and cytopathic effect of HIV-1 in vitro and prolongs life in vivo (see Mitsuya et al, Proc. Natl. Acad. Sci. USA 82, 7096–100, 1985; and Fischl et al, New Engl. J. Med. 317, 185–191, 1987). However, this compound exhibits reversible bone marrow toxicity in a clinical setting (see Yarchoan et al, Lancet 575–580, 1986; Richman et al, New Engl. J. Med. 317, 192–197, 1987). In addition, the development of resistance to AZT is a drawback to its use as an antiviral agent (see Larder et al, Science 243, 1731–1734, 1989). AZT was originally synthesized by Horwitz et al, J. Org. Chem. 29, 2076–2078, 1964. Its activity against Friend leukemia virus (a retrovirus) was reported as early as 1973 (see Ostertage et al, Proc. Natl. Acad. Sci. USA 71, 4980–4985, 1974, and Krieg et al, Exptl. Cell. Res. 116, 21–29, 1978, and references cited therein). The compounds of this invention are structurally unrelated to AZT.

U.S. Pat. No. 4,681,933 describes certain 2',3'-dideoxy-5-substituted uridines and related compounds as antiviral agents. Structurally, these compounds are similar to AZT, and are remote from those of the present invention.

U.S. Pat. No. 4,759,929 discloses a method of treating HIV-1 infection in warm-blooded animals which involves treatment with a salt of 9-antimonio-III-21-tungsten-VI-sodate, $(NH_4^+)_{17}H^+[NaSb_9W_{21}O_{86}]$ (also known as HPA-23). This compound is a polyoxometalate, but it is compositionally different from the compounds of the present invention. Moreover, there are disadvantages associated with this drug, such as: (1) it induces thrombocytopenia and displays, in general, a high toxicity to human bone marrow cells, and (2) it must be taken intravenously as it degrades at pH<4.

Polyoxometalate compounds have also been discovered to have anticoagulant activity. French Patent 2,587,214 is directed to anticoagulant tungstic heteropoly anions for use in vivo and in vitro to prevent blood coagulation.

Polyoxometalates or polyoxoanions are condensed oligomeric aggregates of metal and oxygen atoms that occur in two generic forms: those that contain only these atoms (isopolyoxo anions, isopoly compounds or isos), and those that contain one or more "heteroatoms" in addition to the metal and oxygen atoms (heteropoly anions, heteropoly compounds or heteros). The heteroatoms in the latter class of complexes can be either main group ions, such as $Si^{4+}$ [as in the silicotungstate, $(SiW_{12}O_{40})^{4-}$], $P^{5+}$ [as in the Dawson tungstate, $(P_2W_{18}O_{62})^{6-}$], or transition group ions, such as $Fe^{3+}$ or $Co^{2+}$.

Polyoxometalates have been known for over a century, but only recently has interest in these materials increased. To some degree, this is due to the fact that these materials have become more chemically well defined. In addition, since 1977, the polyoxometalates, and particularly the heteropoly compounds or heteropoly acids, have received increasing attention as reagents or catalysts for redox processes involving organic substrates.

In spite of the known agents for treatment of AIDS, there continues to remain a need for new and effective methods for treatment of retroviral infections, particularly HIV infection, including AIDS and AIDS related complex (ARC). It was in this context that the present invention was accomplished.

SUMMARY OF THE INVENTION

Accordingly, it is an object of the present invention to provide new and effective compositions for treatment of viral infections, particularly retroviral infections.

It is another object of the present invention to provide methods for treatment of viral infections, particularly retroviral infections.

It is yet another object of the present invention to provide compounds and compositions for treatment of AIDS or ARC in mammals, including humans.

These and other objects of the present invention that will hereinafter become more readily apparent, have been accomplished by the discovery that polyoxometalates having the structures identified below exert inhibitory activity towards cells infected with various retroviruses, thereby indicating that these agents will have in vivo activity towards these retroviruses in mammals, including humans.

The present invention is illustrated in detail in the following drawings which are included for illustrative purposes and should not be considered to limit the present invention.

| | |
|---|---|
| $(NH_4^+)_{17}H^+[NaSb_9W_{21}O_{86}]$ | (HPA-23), |
| $(SiW_{12}O_{40})^{4-}$ | (ST), |
| $(BW_{12}O_{40})^{5-}$ | (BT), |
| $(NH_4)_5[BW_{12}O_{40}]$ | (NH4BT), and |
| $(NH_4)_4[SiW_{12}O_{40}]$ | (NH4ST). |

Values shown represent the mean±S.D. of at least 3 determinations.

Figure 7:
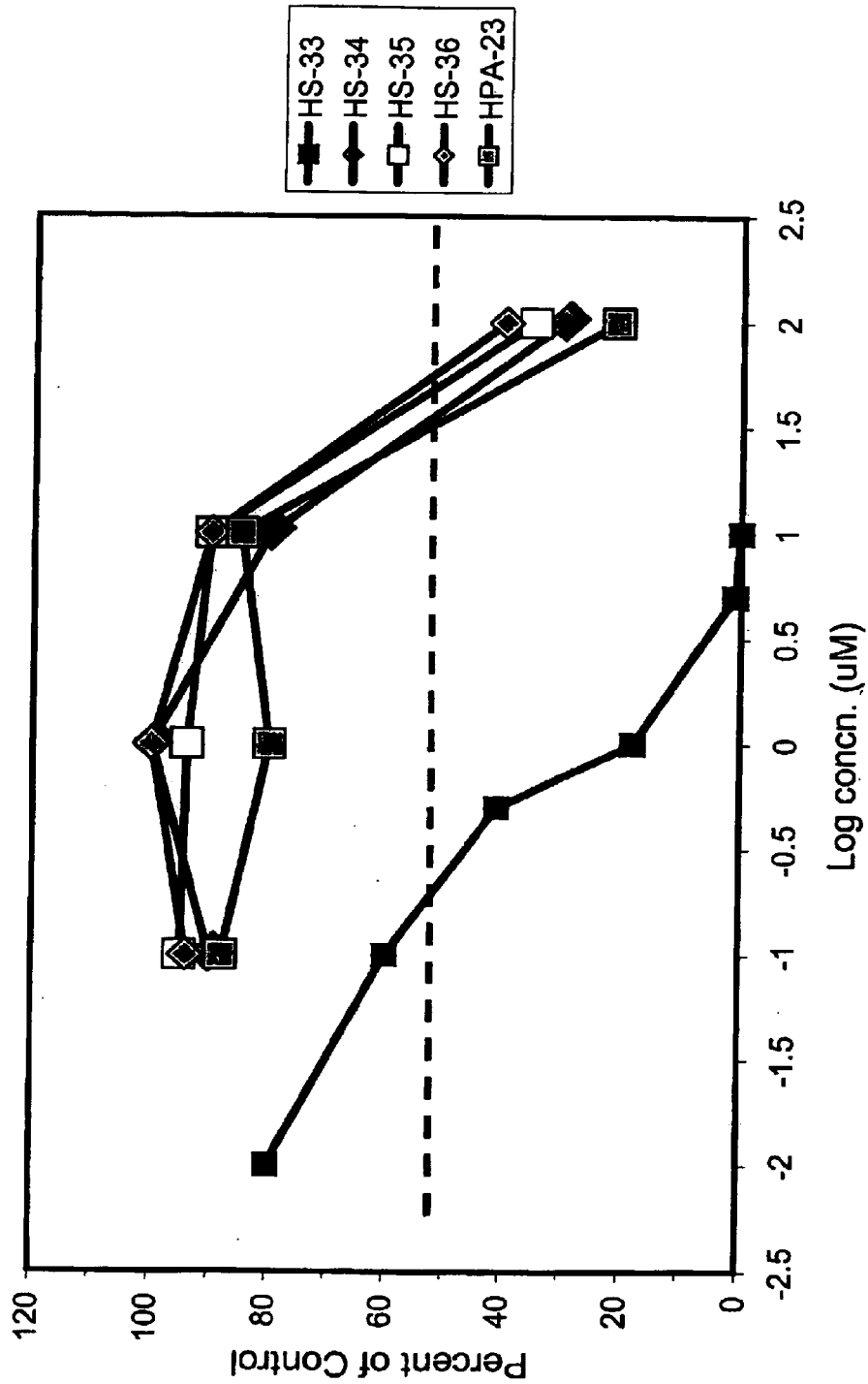

FIG. 7 shows the relative effect of various polyoxometalate compounds on human CFU-GM cells. The polyoxometalate compounds are:

| | |
|---|---|
| $(ArgH^+)_n(H^+)_{5-n}BT$, where $n=1-5$ | (HS-33), |
| $(HisH^+)_p(H^+)_{4-p}ST$, where $p=1-4$ | (HS-34), |
| $(LysH^+)_q(H^+)_{5-q}ST$, where $q=1-5$ | (HS-35), |
| $(ArgH^+)_m(H^+)_{4-m}ST$, where $m=1-4$ | HS-36), | and

| | |
|---|---|
| $(NH_4^+)_{17}H^+[NaSb_9W_{21}O_{86}]$ | (HPA-23). |

DETAILED DESCRIPTION OF THE INVENTION

The polyoxometalates of the present invention may be described by the following generalized formulas:

| | |
|---|---|
| $(X^+)_n(H^+)_{4-n}(SiW_{12}O_{40})^{4-}$ | n = 0 – 4 |
| $(X^+)_m(H^+)_{5-m}(BW_{12}O_{40})^{5-}$ | m = 0 – 5 |
| $(X^+)_p(H^+)_{4-p}(W_{10}O_{32})^{4-}$ | p = 0 – 4 |
| $(X^+)_q(H^+)_{6-q}(P_2W_{18}O_{62})^{6-}$ | q = 0 – 6 | wherein X=K, Na, $NH_4$, histidineH, lysineH, arginineH, and hydrates thereof. X can also be any naturally occurring monocationic amino acid or polypeptide (e.g., 2–10 amino acids, preferably 2–4 amino acids, containing one naturally occurring basic amino acid, i.e., histidine, lysine or arginine, in its protonated and therefore cationic form).

For the sake of simplicity and clarity, the following abbreviations will be used herein-below:

| | | |
|---|---|---|
| $(SiW_{12}O_{40})^{4-}$ | = | ST |
| $(BW_{12}O_{40})^{5-}$ | = | BT |
| $(W_{10}O_{32})^{4-}$ | = | W10 |
| $(P_2W_{18}O_{62})^{6-}$ | = | DT |
| histidine | = | His |
| lysine | = | Lys |
| arginine | = | Arg |

Preferred X groups for the present invention are the naturally occurring protonated basic amino acids histidineH, lysineH and arginineH, and, in particular, arginineH. However, it is also possible that other naturally occurring amino acids or small peptides which are capable of forming a positive charge under neutral or acidic conditions can be useful as cations for purposes of the present invention. Examples of the small peptides are Gly-Arg, Ala-His-Ala, and the like. The small peptides themselves may not occur naturally, but will preferably be based on naturally-occurring amino acids. Naturally-occurring amino acids are generally selected from the 20 naturally-occurring amino acids which are most commonly found in proteins.

The compounds of the present invention may be synthesized by methods known to those of ordinary skill in the art. Both isos, such as W10, and heteros, such as ST, are most often made by carefully acidifying the correct concentrations of monomeric tungstate, usually starting with the sodium salt, $Na_2WO_4$, in aqueous solution, with a water-soluble precursor of the heteroatom, if applicable, followed by precipitation of the product. The appropriate water-soluble salt of the desired cations, $X^+$, is added in the later step or in a subsequent step. In the Example section below, procedures for the preparation of ST, BT and some of the basic amino acid salts of ST and BT are provided.

Specific examples of compounds which fall within the scope of the present invention are the following:

| | |
|---|---|
| $(NH_4)H_3ST$ | $(NH_4)H_4BT$ |
| $(NH_4)_2H_2ST$ | $(NH_4)_2H_3BT$ |
| $(NH_4)_3HST$ | $(NH_4)_3H_2BT$ |
| $(NH_4)_4ST$ | $(NH_4)_4HBT$ |
| $(ArgH)_n(H)_{4-n}ST$, n = 1 – 4 | $(NH_4)_5BT$ |
| $(LysH)_m(H)_{5-m}BT$, m = 1 – 5 | $K_5BT$ |
| $(HisH)_q(H)_{6-q}DT$, q = 1 – 6 | $Na_5BT$ |

Of particular interest are compounds having the formula $(ArgH^+)_n(H^+)_{5-n}BT$, where n=1–5 and $(ArgH^+)_m(H^+)_{4-m}ST$, where m=1–4.

It has been further found that polyoxometalates having the following generalized formulas can be used according to the present invention:

$M_7PW_{11}O_{39}$ $M_8SiW_{11}O_{39}$ $M_9HSiW_9O_{34}$ $M_8HPW_9O_{34}$ $M_{10}(TM)_4(PW_9O_{34})_2$ $M_{16}(TM)_4(P_2W_{15}O_{56})_2$ $M_{14}[NaP_5W_{30}O_{110}]$ $M_{12}(TM)_3(PW_9O_{34})_2$ $M_6P_2W_{18}O_{62}$ wherein M is an alkali metal, $NH_4^+$ or other common monocation or soluble dication, or any combination of the above provided adequate water solubility is exhibited, or histidinium ion, argininium ion, or lysinium ion or any dication of a dipeptide or oligopeptide with 2 protonated basic amino acid residues, or any combination of these monocations or dications with each other or with any common inorganic cation, and TM is a divalent transition metal ion, such as Mn, Fe, Co, Ni, Cu and Zn.

Specific examples of compounds which fall within the scope of the present invention are the following:

$Na_7PW_{11}O_{39}$ $K_8SiW_{11}O_{39}$ $Na_9HSiW_9O_{34}$ $Na_8HPW_9O_{34}$ $K_{10}Cu_4(H_2O)_2(PW_9O_{34})_2$ $K_{10}Co_4(H_2O)_2(PW_9O_{34})_2$ $(NH_4)_{14}[NaP_5W_{30}O_{110}]$ $H_6P_2W_{18}O_{62}$ $(NH_4)_6P_2W_{18}O_{62}$

In order to evaluate their anti-HIV-1 activity and toxicity, twenty-one known polyoxometalate compounds (18 polyoxotungstates in several structural classes), were evaluated in human PBM cells. The formulas and molecular weights of these compounds, along with their $EC_{50}$ and 50% inhibitory concentration ($IC_{50}$) values, are shown in Table 1 below.

TABLE 1

Anti-HIV-1 Activity and Toxicity of Seven Structural Categories of Polyoxometalates in Human PBM Cells

| | Molecular formula of compound | Mol. Wt. | $EC_{50}$, $\mu M$ | $IC_{50}$, $\mu M$ |
|---|---|---|---|---|
| | Structural class: HPA-23 | | | |
| 1 | $(NH_4)_{17}Na[NaSbgW_{21}O_{86}]$ | 6,940 | 0.39 | 35 |
| | Structural class: "Keggin" | | | |
| 2 | $H_3PW_{12}O_{40}$ | 2,988 | 14.0 | >100 |
| 3 | $H_4SiW_{12}O_{40}$ | 3,004 | 0.12 | >200 |
| 4 | $H_5BW_{12}O_{40}$ | 3,042 | 0.46 | 126 |
| 5 | $H_6ZnW_{12}O_{40}$ | 3,097 | 0.90 | 12 |
| 6 | $Na_6H_2W_{12}O_{40}$ | 2,986 | 0.34 | >100 |
| 7 | $[(DMA)_2H]_3PMo_{12}O_{40}{}^a$ | 2,348 | >100 | >100 |
| | Structural class: "Keggin" lacunary | | | |
| 8 | $Na_7PW_{11}O_{39}$ | 3,081 | 10.8 | >100 |
| 9 | $K_8SiW_{11}O_{39}$ | 2,987 | 0.15 | >100 |
| | Structural class: trivacant "Keggin" fragment | | | |
| 10 | $Na_9HSiW_9O_{34}$ | 2,849 | 2.4 | >100 |
| | Structural class: Bis-trivacant "Keggin" fragment sandwich (BTKS) | | | |
| 11 | $K_{10}Cu_4(H_2O)_2(PW_9O_{34})_2$ | 5,464 | 4.4 | >100 |
| 12 | $K_{10}Co_4(H_2O)_2(PW_9O_{34})_2$ | 5,482 | 0.8 | 44 |
| | Structural class: "Wells-Dawson" | | | |
| 13 | $H_6P_2W_{18}O_{62}$ | 4,763 | 0.52 | 6.2 |
| 14 | $(NH_4)_6P_2W_{18}O_{62}$ | 4,865 | 0.91 | 1.8 |
| | Structural class: "Lindqvist" | | | |
| 15 | $(n-Bu_4N)_2W_6O_{19}$ | 1,892 | 107 | >100 |
| 16 | $(n-Bu_4N)_2Mo_6O_{19}$ | 1,365 | >100 | >100 |
| | Structural class: "Preyssler" | | | |
| 17 | $(NH_4)_{14}[NaP_5W_{30}O_{110}]$ | 8,264 | 0.32 | 7.7 |
| | Structural class: Decatungstate | | | |
| 18 | $(NH_4)_4W_{10}O_{32}$ | 2,423 | 1.8 | 115 |
| 19 | $(Me_4N)_4W_{10}O_{32}$ | 2,648 | 3.1 | >100 |
| | Structural class: Miscellaneous | | | |
| 20 | $\alpha\text{-}(n-Bu_4N)_4Mo_8O_{26}$ | 2,153 | 55.3 | >100 |
| 21 | $K_4W_4O_{10}(O_2)_6$ | 1,352 | >50 | >100 |
| | AZT (zidovudine) - non polyoxometalate anti-HIV-1 agent | | | |
| 22 | $C_{10}H_{13}N_5O_3$ | 267 | 0.004 | >100 |

${}^a$DMA = N,N-Dimethyl acetamide.

The compounds in the lacunary and trivacant fragment structural classes (see Table 1, Formulas 8, 9 and 10, respectively) are known to be derived from the "Keggin" structural class (Formulas 2–7 in Table 1). The compounds in the fifth structural class, the bis-trivacant "Keggin" fragment sandwich (BTKS) compounds, are derived from the trivacant species in the fourth structural class. The structural and chemical relationships between the compounds in the remaining structural categories are complicated and not well established.

The following points regarding the anti-HIV-1 activity of the polyoxometalate compounds were observed. First, none of the complexes containing 8 or fewer metal ions (Formulas 15, 16, 20, and 21 in Table 1) have marked activity; all have $EC_{50}$ values>50 $\mu M$. In contrast, the remaining 17 polyoxometalate compounds, with the exception of the Keggin polyoxomolybdate (Formula 7), have demonstrable activity. Of this group, all but two have $EC_{50}$ values below 10 $\mu M$, and ten have $EC_{50}$ values at or below 1 $\mu M$.

Furthermore, the activity of five of the compounds is as high or higher than that of HPA-23, and none is as potent as AZT (Control Formula 22 in the Table).

In addition, it was observed that although there appears to be some correlation with the size, shape, or molecular charge of the polyoxometalates and their anti-HIV-1 activity, the correlation is not a strong one.

Examination of the data in Table 1 also established that the toxicity of most of the polyoxometalates in PBM cells was not very high. The therapeutic indices in these human cells was quite high for several of the compounds. Some of the compounds had higher therapeutic indices than that of $(NH^{4+})_{17}(H^+)(NaSb_9W_{21}O_{86}{}^{18-})$, or HPA-23. The highest was observed with Compound 3 in Table 1, also referred to as silicotungstic acid or ST, despite the well known acidity of this compound.

As noted above, the compounds of the invention may be synthesized by methods known to those of ordinary skill in the art. More specifically, "Keggin" lacunary compounds having the formula $M_7PW_{11}O_{39}$ can be prepared, for example, according to the method disclosed in Brevard et al, J. Am. Chem. Soc. 105, 7059, 1983. $K_8SiW_{11}O_{39}$ can be prepared, for example, using the procedure described in Tézé et al, J. Inorg. Nucl. Chem. 39, 999, 1977. $Na_2HSiW_9O_{34}$ can be prepared, for example, according to the procedure detailed in Hervé et al, Inorg. Chem. 16, 2115, 1977. Compounds having the formula $M_8HPW_9O_{34}$ (the analogue of $M_9HSiW_9O_{34}$, but with $P^{5+}$ in place of $Si^{4+}$) can be prepared, for example, using the procedure disclosed in Finke et al, Inorganic Chem. 26, 3886, 1987. "Keggin" trivacant fragment sandwich compounds having the formula $M_{10}(TM)_4(PW_9O_{34})_2$ can be prepared, for example, according to the procedure described in footnote 10 of Finke et al, J. Am. Chem. Soc. 103, 1587, 1981. Compounds having the formula $M_{16}(TM)_4(P_2W_{15}O_{56})_2$, the analogue of $M_{10}(TM)_4(PW_9O_{34})_2$, but with $(P_2W_{15}O_{56})$ in place of $(PW_9O_{34})$, can be prepared, for example, according to the procedure detailed in Finke et al, Inorganic Chem. 26, 3886, 1987. "Preyssler" compounds having the formula $M_{14}[NaP_5W_{30}O_{110}]$ can be prepared, for example, using the method of Alizadeh, J. Am. Chem. Soc. 107, 2662, 1985. Compounds having the formula $M_{12}(TM)_3(PW_9O_{34})_2$ can be prepared, for example, according to the method of Knoth et al, Inorganic Chem. 25, 1577, 1986.

As used in this invention, antiviral activity refers to the ability of a compound to inhibit the growth of a virus in vitro or in vivo. The viruses of particular interest in the present application are HIV-1, HIV-2, herpes simplex virus type 1 (HSV-1) and type 2 (HSV-2), and simian immunodeficiency virus (SIV). Of particular importance are HIV-1 and HIV-2, particularly HIV-1. However the present compounds may also exhibit antiviral activity towards other retroviruses, such as two murine retroviruses (EY10 and Cas-Br-M), and other viruses in general, such as viruses of the herpes family, including herpes simplex viruses type 1 and 2 (mentioned above) and cytomegaloviruses. The compounds may also have antimicrobial properties.

Humans suffering from diseases caused by, for example, HIV can be treated by administering to the patient a pharmaceutically effective amount of one or more of the present compounds, optionally, but preferably in the presence of a pharmaceutically acceptable carrier or diluent. There may also be included pharmaceutically compatible binding agents, and/or adjuvant materials. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form. For injection purposes, the medium used will be a sterile liquid. As an injection medium, it is preferred to use water which contains the stabilizing agents, solubilizing agents and/or buffers conventional in the case of injection solutions. Desirable additives include, for example, tartrate and borate buffers, ethanol, dimethyl sulfoxide, complex forming agents (for example, ethylene diamine tetraacetic-acid), high molecular weight polymers (for example, liquid polyethylene oxide) for viscosity regulation or polyethylene derivatives of sorbitan anhydrides.

Solid carrier materials include, for example, starch, lactose, mannitol, methyl cellulose, talc, high dispersed silicic acid, high molecular weight fatty acids (such as stearic acid), gelatin, agar-agar, calcium phosphate, magnesium stearate, animal and vegetable fats or solid high molecular weight polymers (such as polyethylene glycols). Compositions suitable for oral administration can, if desired, contain flavoring and/or sweetening agents.

A preferred mode of administration of the compounds of this invention is oral administration. Accordingly, the compounds may be formulated into tablet form.

The active materials according to the present invention can be employed in dosages and amounts which are determined by conventional methods in the art of pharmacology. Thus, the materials can be used at a dosage range in humans of from 0.1 to 100 mg/kg total body weight/day. A more preferred range lies between 1 to 30 mg/kg total body weight/day. A most preferred range is 1 to 20 mg/kg total body weight/day. The dosages may be administered at once, or may be divided into a number of smaller doses to be administered at varying intervals of time.

The compounds of the present invention are expected to be useful in treating mammals, including humans. Other mammals include dogs, cats, monkeys, horses, and the like.

In order to be useful, the compounds should exhibit relatively low toxicity towards normal cells. The toxicities of some of the present compounds were measured in Vero cells and human peripheral blood mononuclear cells, and toxicity values were determined. The toxicity tests are described below.

The invention now being generally described, the same will be better understood by reference to certain specific Examples which are included herein for the purposes of illustration only and are not intended to limit the invention or any embodiment thereof, unless specified.

EXAMPLE 1

Synthesis of Representative Compounds

I. $H_4SiW_{12}O_{40}$ (1). Pope, Michael Thor, *Heteropoly and Isopoly Oxometalates*, Springer-Verlag, Berlin, p. 1, 1983.

A solution of $Na_2WO_4.2H_2O$ was made by dissolving 25 g of the compound in 125 ml of deionized water with stirring in a 250 ml round-bottomed flask. Then 1.25 ml of sodium silicate solution, $NaSiO_3$ saturated in water (water glass) was added and the resulting mixture was heated to 80° C. for 5 minutes. At this point, 15 ml of concentrated HCl was added over 1.5 hours, using a dropping funnel, to the hot, stirring, solution. The solution was then taken off the heat and transferred to a separatory funnel, where it was allowed to cool for 15 minutes. The addition of 10 ml HCl and 50 ml of $Et_2O$ resulted in the formation of three layers. The top two layers were clear, the top layer being ether and the next lower layer being the water layer. There was then a murky white, ill-defined border of unknown composition which was probably a mixture of that layer and the lowest layer. The lowest layer was a clear viscous fluid which was the etherate which contained the product. The layers were each drawn off and the etherate layer was allowed to sit overnight at room temperature (RT) and form crystals. These crystals were recrystallized from water and the white crystalline product, 14 g, was characterized by infrared spectroscopy (IR), ultraviolet spectroscopy (UV) and tungsten nuclear magnetic resonance ($^{183}$W NMR). These spectra were characteristic for the compound.

II. Synthesis of Amino Acid Salts: Lysinium, Argininium, and Histididium, from (1).

A. Lysinium Salt: (2)

This procedure was adapted from the E. O. North procedure for the sodium salt. A saturated solution of (1) in water was prepared using 3.6 g in a minimal amount of water. A saturated solution of lysine monohydrochloride (from Aldrich) using 1 g in a minimal amount of water was then prepared. The lysine solution was then added to the solution of (1) with stirring. The addition resulted in a bright white precipitate, whose polyoxometalate nature was qualitatively confirmed by a quick color change to blue when a small amount was exposed to a metal spatula for a few minutes. The precipitate was vacuum-filtered off and a small amount vacuum-dried at 40° C. An IR of the dried material (1 part compound:35 parts KBr) showed the presence of the characteristic set of peaks of(1) as well as several peaks which were due to a lysine countercation. Recrystallization of the compound was effected by dissolving the compound in water with low heat and allowing the solution to sit at room temperature until crystals formed. After several days, blue-white gelatinous clumps formed. The clumps became a chunky white powder when vacuum-filtered. Using the same recrystallization clumps which became white microcrystals when filtered off by a vacuum. The $^1$H NMR of the product confirmed the presence of lysine (by comparison of the spectra to reported spectra). An IR also showed the presence of characteristic peaks for lysine. HCl as well as the reference peaks expected for the anion of (1).

B. Argininium Salt: (3)

The same general procedure was used for the preparation of this salt as was used for the preparation of (2) with a substitution of arginine monohydrochloride (from Alfa) for the countercation. In contrast to the lysine salt, the white precipitate formed only after the addition of 3 ml of the saturated solution rather than immediately. Due to this slower precipitate formation, the solution was allowed to stir for 1 hour before vacuum filtration removed the crude product. This material (3 g) was recrystallized from 25 ml of water. While most of the compound remained undissolved after sonication and stirring at low heat, the filtrate was collected and left to sit at room temperature for several days. White crystals formed and were collected (0.5 g). The IR spectrum of the product indicated both the characteristic peaks for the anion of (1) and the peaks for the argininium countercation. The $^1$H NMR showed an almost identical peak pattern as that which was seen for the starting material of the argininium countercation.

C. Histidinium Salt: (4)

The same general procedure was followed in this preparation as was used in the synthesis of (2) with the substitution of histidine hydrochloride (from Alfa) for the countercation source. A saturated solution of (1) was prepared by dissolving 4 g of it in a minimal amount of water. A saturated solution of histidine hydrochloride in water was prepared and was added dropwise to the solution of (1). During initial additions, brief flashes of white ppt appeared and quickly redissolved. As more of the countercation solution was added (approx. 2 ml) the ppt became permanent and upon addition of an additional ml of solution, the resulting solution was allowed to stir for an hour and the precipitate produced vacuum-filtrated off. Recrystallization was effected by treatment of 1.71 g with 200 ml water. While some of the compound remained insoluble, the filtrate was collected and allowed to sit until white microcrystals formed. The IR and $^1$H NMR of the final product were consistent with the compound's components.

III. Synthesis of K$_5$BW$_{12}$O$_{40}$ (5):

The following were added successively to 100 ml of water with vigorous stirring: 50 g of Na$_2$WO$_4$.2H$_2$O, 2.5 g H$_3$BO$_3$, and 30 ml 6 M HCl. The resulting solution, approx. pH 6, was allowed to boil for 8 hours. Water was added from time to time as needed. Any solid formed during this time, beta-paratungstate (Na$_{10}$W$_{12}$O$_{42}$.xH$_2$O), was filtered off. The solution was then acidified to pH 2 with 6 M HCl and boiled for an additional 30 minutes. Precipitation was effected using 10 g solid KCl. After filtration and a diethyl ether wash, the crude product was recrystallized at 60° C. in 25 ml water. An IR of the product was identical to the literature spectrum of the compound.

IV. Synthesis of Amino Acid Salts: Lysinium, Argininium, and Histidinium, from (5).

A. Lysinium Salt (6):

The same general procedure was used for this synthesis as was used for the amino acid salts of (1). A solution of (5) was prepared by dissolving/suspending 1.3 g in 25 ml water. This produced a cloudy liquid. A saturated solution of lysine hydrochloride in water was also prepared. This solution was added dropwise to the solution/suspension of (5) with stirring. During addition, the solution gradually became clearer with each drop added and the cloudiness disappeared altogether after the addition of 20 ml. The solution was allowed to sit until white, roundish globules formed. These were filtered off, redissolved in water, and allowed to sit and recrystallize. Clear polyhedrons came out of solution 10 days later (0.8 g). IR and $^1$H NMR were used to characterize the compound. The IR indicated the presence of both the anion of (5) as well as the lysinium countercation. The $^1$H NMR gave better proof that the lysinium countercation was present by the comparison of the spectra with literature spectra of lysine hydrochloride and with the spectra of the starting materials.

B. Synthesis of X$_5$BW$_{12}$O$_{40}$ where X is NH$_4^+$, Na$^+$, ArginineH$^+$, and HistidineH$^+$, from H$_5$BW$_{12}$O$_{40}$ (5).

These derivatives were prepared using (5) in aqueous solution. The different salts were prepared by acidification of the (5) solution by addition of 6M HCl to pH 1.4. The solution was then separated into 5 equal aliquots. At this point, the countercation saturated aqueous solutions were added until pH 2.3 was attained. The solutions remained undisturbed for 30 minutes and the various precipitates filtered.

1. X is ArginineH$^+$ (7):

A saturated aqueous solution of arginine hydrochloride was added as the countercation source and a yield of 3.6 g of white precipitate was produced. This was characterized by IR and $^1$H NMR, and the spectra were consistent with the compound's components.

2. X is HistidineH$^+$ (8):

A saturated aqueous solution of histidine hydrochloride was added as the countercation source and a yield of 3.7 g of white precipitate was produced. The compound was characterized by IR and $^1$H NMR, and the spectra were consistent with the compound's components.

EXAMPLE 2

Biological Activity

At present, there are no available animal models for HIV-1. Chimpanzees can be infected but do not develop disease. Therefore, in general, in vitro activity towards infected cells is reported hereinbelow.

Cells. Human peripheral blood mononuclear cells (PBMC) from healthy HIV-1 seronegative and hepatitis B virus seronegative donors were isolated by Ficoll-Hypaque discontinuous gradient centrifugation at 1,000×g for 30 minutes, washed twice in phosphate-buffered saline (pH 7.2; PBS), and pelleted at 300×g for 10 minutes. Before infection, the cells were stimulated by phytohemagglutinin (PHA) at a concentration of 6 μg/ml for three days in RPMI 1640 medium supplemented with 15% heat-inactivated fetal calf serum, 1.5 mM L-glutamine, penicillin (100 U/ml), streptomycin (100 μg/ml), and 4mM sodium bicarbonate buffer.

Viruses. HIV-1 (strain LAV-1) was obtained from Dr. P. Feorino (Centers for Disease Control, Atlanta, Ga.). The virus was propagated in human PBMC using RPMI 1640 medium, as described previously (McDougal et al, J. Immun. Meth. 76, 171–183, 1985) without PHA and supplemented with 7% v/v interleukin-2 (Advanced Biotechnologies, Silver Spring, Md.), 7 μg/ml DEAE-dextran (Pharmacia, Uppsala, Sweden), and 370 U/ml anti-human leucocyte (alpha) interferon (ICN, Lisle, Ill.). Virus obtained from cell-free culture supernatant was titrated and stored in aliquots at −80° C. until use.

Inhibition of virus replication in human PBMC. Uninfected PHA-stimulated human PBMC were uniformly distributed among 25 cm$^2$ flasks to give a 5 ml suspension containing about 2×10$^6$ cells/ml. Suitable dilutions of virus were added to infect the cultures. The mean reverse transcriptase (RT) activity of the inocula was 50,000 decompositions per min/ml corresponding to about 100 TCID$_{50}$, as determined by Groopman et al. (Groopman et al, AIDS Res. Human Retro. 3, 71–85, 1987. The drugs at twice their final concentrations in 5 ml of RPMI 1640 medium, supplemented as described above, were added to the cultures. Uninfected and untreated PBMC at equivalent cell densities were grown in parallel as controls. The cultures were maintained in a humidified 5% CO$_{2-95}$% air incubator at 37° C. for six days after infection, at which point all cultures were sampled for supernatant reverse transcriptase (RT) activity. Previous studies had indicated that maximum RT levels were obtained at that time.

RT activity assay. Six ml supernatant from each culture was clarified from cells at 300×g for 10 minutes. Virus particles were pelleted from 5 ml samples at 40,000 rpm for 30 minutes using a Beckman 70.1 Ti rotor and suspended in 200 μl of virus disrupting buffer (50 mM Tris-Cl, pH 7.8, 800 mM NaCl, 20% glycerol, 0.5 mM phenylmethyl sulfonyl fluoride, and 0.5% Triton X-100).

The RT assay was performed in 96-well microtiter plates, as described by Spira et al. (Spira et al, J. Clin. Microbiol. 22, 97–99, 1987). The reaction mixture, which contained 50 mM Tris-Cl pH 7.8, 9 mM MgCl$_2$, 5 mM dithiothreitol (DTT), 4.7 μg/ml (rA)$_n$·(dT)$_{12-18}$, 140 μM dATP, and 0.22 μM [$^3$H]TTP, specific activity 78.0 Ci/mmol, equivalent to 17,300 cpm/pmol; NEN Research Products, Boston, Mass., was added to each well. The sample (20 μl) was added to the reaction mixture which was then incubated at 37° C. for 2 hours. The reaction was terminated by the addition of 100 μl 10% trichloroacetic acid (TCA) containing 0.45 mM sodium pyrophosphate. The acid-insoluble nucleic acids which precipitated were collected on glass filters using a Skatron semi-automatic harvester. The filters were washed with 5% TCA and 70% ethanol, dried, and placed in scintillation vials. Four ml of scintillation fluid (Econofluor, NEN Research Products, Boston, Mass.) were added and the amount of radioactivity in each sample was determined using a Packard Tri-Carb liquid scintillation analyzer (model 2,000CA). The results were expressed in dpm/ml of original clarified supernatant.

Cytotoxicity assay. The drugs were evaluated for their potential toxic effects on uninfected PHA stimulated human PBMC. Flasks were seeded so that the final cell concentration was 2×10$^5$ cells/ml. The cells were cultured with and without drug for 6 days, at which time aliquots were counted for cell viability, as assessed by the trypan blue dye-exclusion method using a hemacytometer. The median inhibitory concentration (IC$_{50}$) was calculated using the median effect method (Chou et al, Elsevier-Biosoft, Elsevier Science Publishers, Cambridge, U.K., 1985; Chou et al, Adv. Enz. Regul. 22, 27–55, 1984).

Evaluation of compounds on purified retroviral RT. HIV-1 RT was isolated from detergent disrupted virions obtained from the cell-free supernatant of infected PHA-stimulated PBMC. The enzyme was purified by passing the extract through ion-exchange chromatography columns, as described previously (Eriksson et al, Antimicrob. Agents Chemother. 31, 600–604, 1977. Briefly, 750 ml of culture fluid harvested from HIV-1-infected PBMC were ultracentrifuged to pellet the virus. The pellet was dissolved in buffer A [50 mM Tris-HCl, pH 7.9/0.25% Nonidet P-40/5 mM dithiothreitol/20% (vol/vol) glycerol] containing 1 mM EDTA, and freeze-thawed four times. After clarification by centrifugation, the enzyme was partially purified from the supernatant by passing the extract through a DEAE-cellulose column (Whatman DE-52; 2.6×15 cm) previously equilibrated with buffer B (50 mM Tris-Cl, pH 7.9, 50 mM KCl, 1 mM EDTA, 1 mM dithiothreitol, 20% glycerol). Elution was performed using a linear gradient 50–500 mM KCl in buffer B. Fractions containing enzyme activity were dialyzed against buffer B and were further purified on a phosphocellulose column (Whatman P-11) using a linear KCl (50–500 mM) gradient in buffer B. The peak fractions were pooled and dialyzed against buffer B. The enzyme was characterized as HIV-1 reverse transcriptase based on its cation, salt, pH, and template requirements according to previous descriptions (Eriksson et al, Antimicrob. Agents Chemother. 31, 600–604, 1977). The standard reaction mixture was used to evaluate the inhibitory effect of the drugs, as previously described (Eriksson et al, Antimicrob. Agents Chemother. 31, 600–604, 1977). Briefly, the reaction mixtures (final volume 100 μl) contained 100 mM Tris-HCl, pH 8.0, 50 mM KCl, 2 mM MgCl$_2$, 5 mM DTT, 400 ug/ml bovine serum albumin, 3 μg/ml (rA)·(dT)$_{12-18}$ and 1 μM of [$^3$H]TTP (specific activity 82.3 Ci/mmol). The reactions were started by the addition of 10 μl of partially purified RT, incubated at 37° C. for 60 min., and processed as previously described (Eriksson et al, Antimicrob. Agents Chemother. 31, 600–604, 1977).

Cell culture assays for heroes simplex viruses. Mycoplasma-free Vero cells, obtained from Flow Laboratory (McLean, Va.), were used for the plaque assays. The methodologies for the plaque reduction and cytotoxicity assays have been previously described (Schinazi et al, Antimicrob. Agents Chemother. 22, 499–507, 1982).

Median-effect method. Dose-effect relationships were analyzed by the median-effect equation (Chou et al, Adv.

Enz. Regul. 22, 27–55, 1984). The slope (m) and median effective and inhibitory concentration ($EC_{50}$ and $IC_{50}$) values were obtained by using a computer program developed by Chou and Chou (Chou et al, Elsevier-Biosoft, Elsevier Science Publishers, Cambridge, U.K., 1985).

UV/XC Assay for Murine Retroviruses Cells. Mouse embryo fibroblasts (SC-1) and XC cells were obtained from the American Type Culture Collection, Rockville, Md. The XC cell line was derived from a transplantable tumor induced in newborn White-Weston rats by the intramuscular injection of the Prague strain of Rous sarcoma virus. This cell line does not release infectious virus. The cells were maintained in Eagle's minimum essential medium with Hanks balanced salt solution, supplemented with penicillin (100 U/ml), streptomycin (100 µg/ml), sodium bicarbonate (24 mM), Hepes (25 mM), and either 2 (maintenance) or 10 (growth) percent inactivated newborn or fetal calf serum.

Virus quantitation by UV-XC assay. The XC test (Rowe et al, Virology 42, 1136–1139, 1970) is a plaque-type of assay which tests for the presence and titer of B- and N-tropic murine leukemia viruses. Because these viruses produce no overt signs of infection of SC-1 mouse cells, it is necessary to overlay the virus producing culture with an indicator cell line, XC. The number of syncytia that are produced is a direct measure of the virus titer in FFU.

Six-well plates were seeded with $1 \times 10^5$ SC-1 mouse cells on the first day. On the following day the medium was removed and the inoculum (0.2 ml) was added in medium containing polybrene (4 µg/ml). For determining the antiviral activity of the compounds in culture, the virus dilution selected produced in untreated cultures about 80 foci per well. After 1 hour, the virus was removed and various concentrations of the drug were added. The plates were replenished with medium on the third and fifth days. The medium was removed on the eighth day and the cells exposed to UV irradiation (60 erg/mm$^2$ per sec) for 30 seconds. Medium containing $10^6$ XC cells was then added to each plate. On the eleventh day, the plates were fixed with 10% buffered Formalin and stained with crystal violet. Comparison of the number of foci to those found in virus-infected cells receiving no drug allowed determination of whether a drug at a particular concentration was effective. Control cells without virus but receiving the drug provided an estimate of the drug's toxic effects as quantitated by using trypan blue staining.

Bone Marrow Toxicity Assays

Preparation of Cells. Human bone marrow cells were collected by aspiration from the posterior iliac crest of normal healthy volunteers, treated with heparin and the mononuclear population separated by Ficoll-Hypaque gradient centrifugation. Cells were washed twice in Hanks balanced salt solution, counted with a hemacytometer and their viability was >98% as assessed by trypan blue exclusion.

Assay of Colony-Forming Unit Granulocyte-Macrophage (CFU-GM) for Drug Cytotoxicity. The culture assay for CFU-GM was performed using a bilayer soft-agar method as recently described (Sommadossi et al, Antimicrob. Agents Chemother. 31, 452–454, 1987). McCoy 5A nutrient medium supplemented with 15% dialyzed fetal bovine serum (heat inactivated at 56° C. for 30 min.) (Gibco Laboratories, Grand Island, N.Y.) was used in all experiments. This medium was completely lacking in thymidine and uridine. Cells were cloned in 0.3% agar in the presence of increasing concentrations of the modulating compound or in medium alone (control). After 14 days of incubation at 37° C. in a humidified atmosphere of 5% $CO_2$ in air, colonies ($\geq 50$ cells) were counted using an inverted microscope.

Bone Marrow Toxicity Studies

Figure 1:
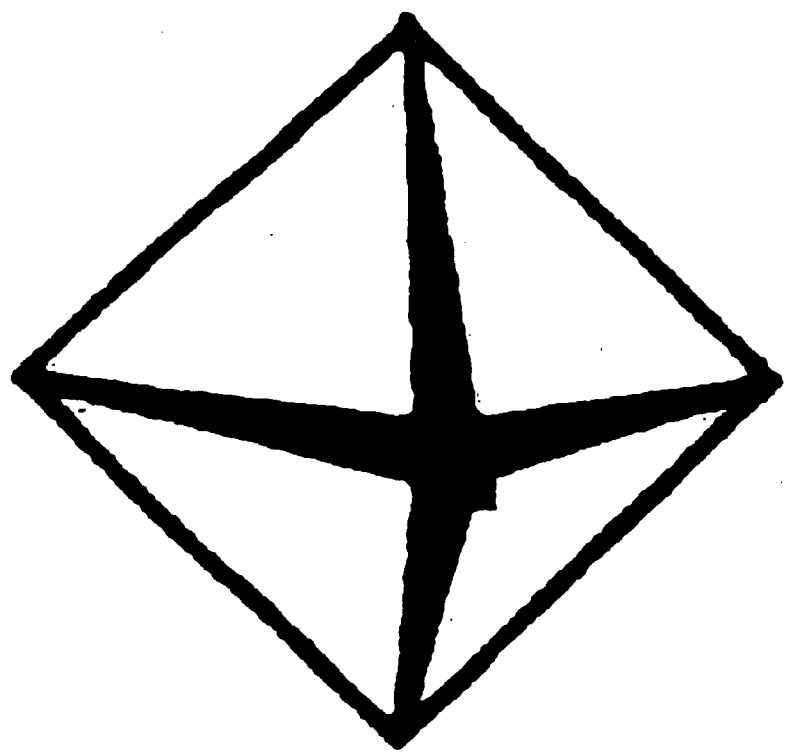
FIG. 1 shows the diamond, or octahedral, structural subunit of the four representative structural types of polyoxotungstates represented in FIGS. 2 through 5. Each structural subunit represents one tungsten atom surrounded by six oxygen atoms.
Figure 2:
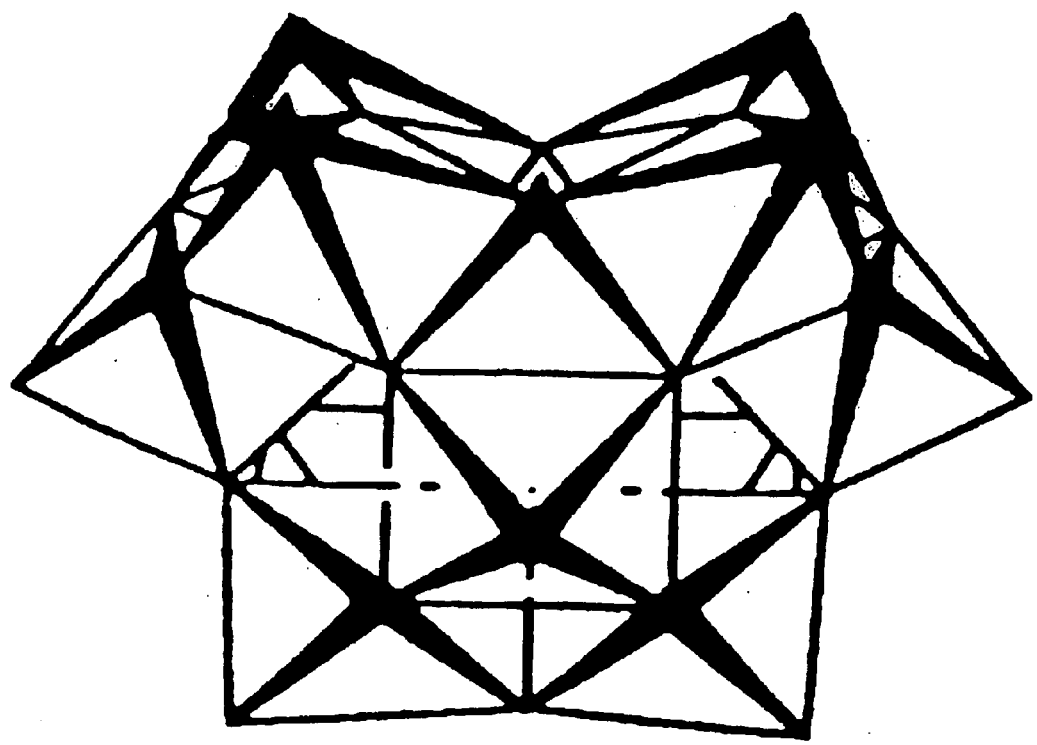
FIG. 2 shows the "Keggin" structure. The molecular formula is $(X^{n+}W_{12}O_{40})^{(8-n)-}$ ($T_d$ molecular point group symmetry). Borotungstate, or $(BW_{12}O_{40})^{5-}$, is when $X^{n+}=B^{3+}$; silicotungstate, or $(SiW_{12}O_{40})^{4-}$, is when $X^{n+}=Si^{4+}$.
Figure 3:
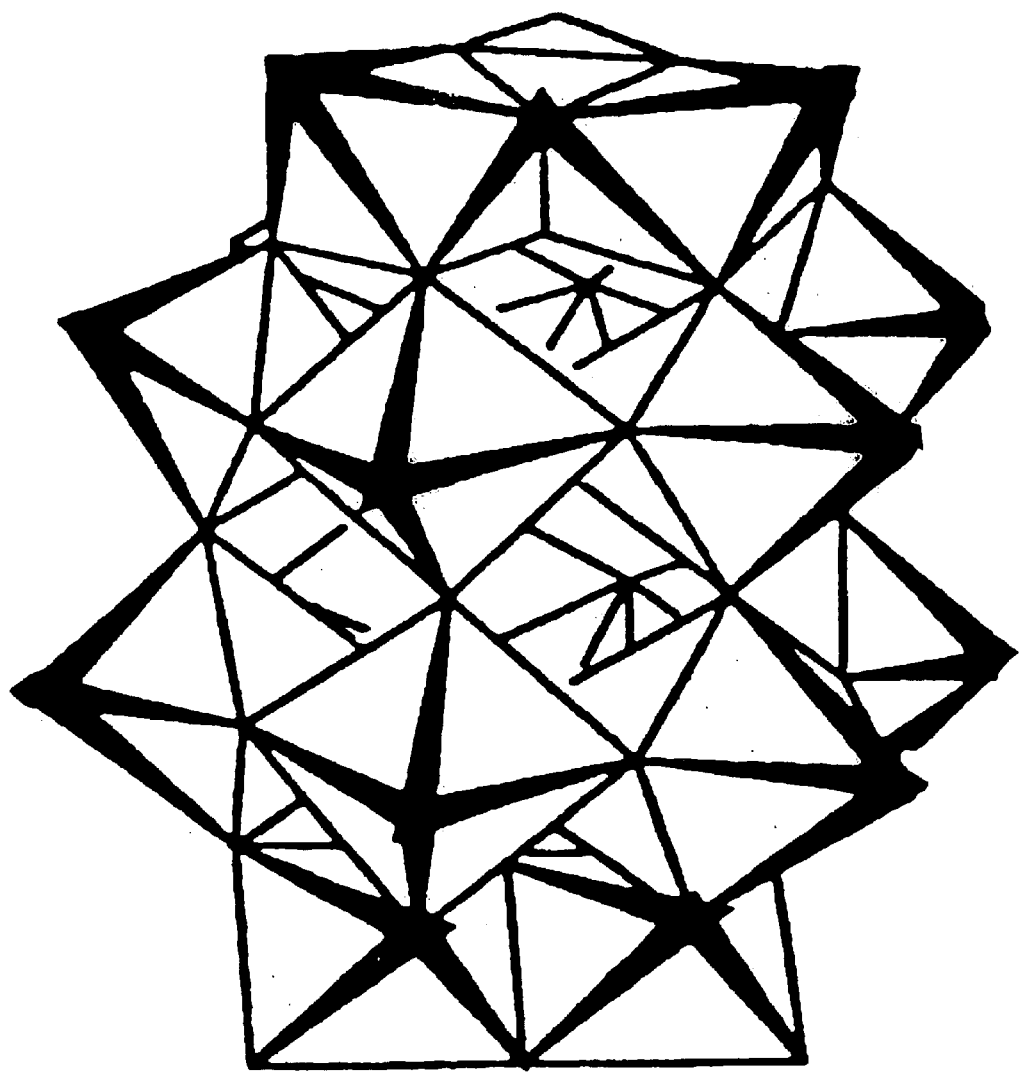
FIG. 3 shows the "Dawson" or "Wells-Dawson" structure. The molecular formula is $(P_2W_{18}O_{62})^{6+}$ (the predominant isomer is $D_{3h}$ molecular point group symmetry).
Figure 4:
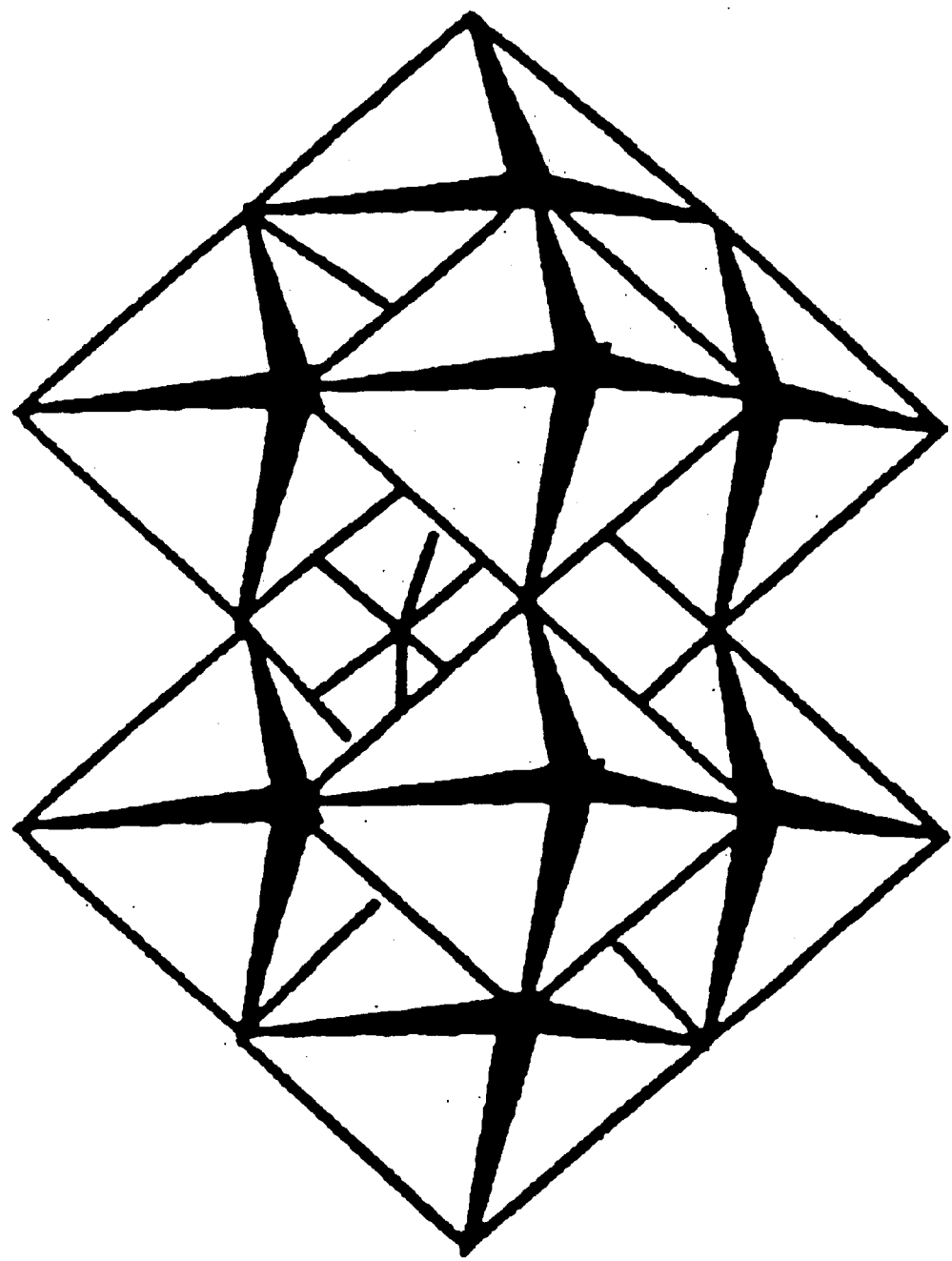
FIG. 4 shows the decatungstate structure. The molecular formula is $(W_{10}O_{32})^{4-}$ ($D_{4h}$ molecular point group symmetry).
Figure 5:
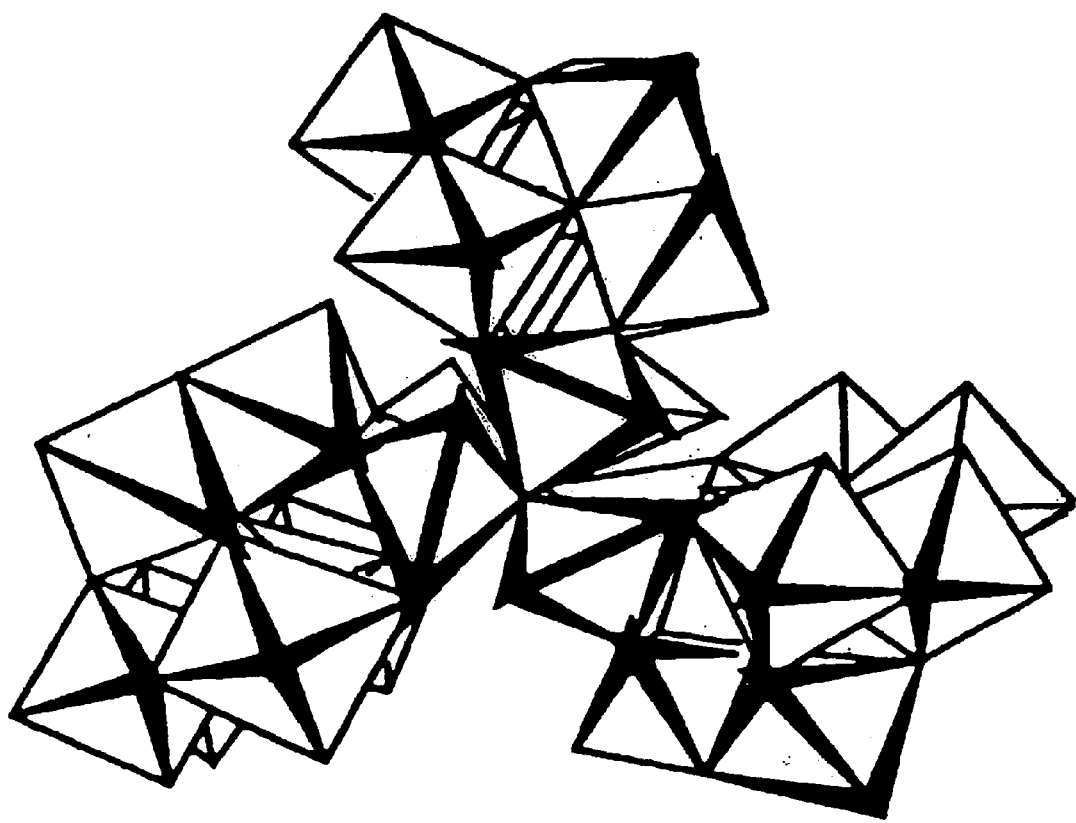
FIG. 5 shows the 9-antimonio(III)-21-tungsten(VI)-sodate structure. The molecular formula is $[NaSb_9W_{21}O_{86}]^{18-}$ ($C_{3h}$ molecular point group symmetry). The 17 ammonium, monosodium (or hydrogen) salt of this complex structure is the French anti-HIV-1 agent, HPA-23.
Figure 6:
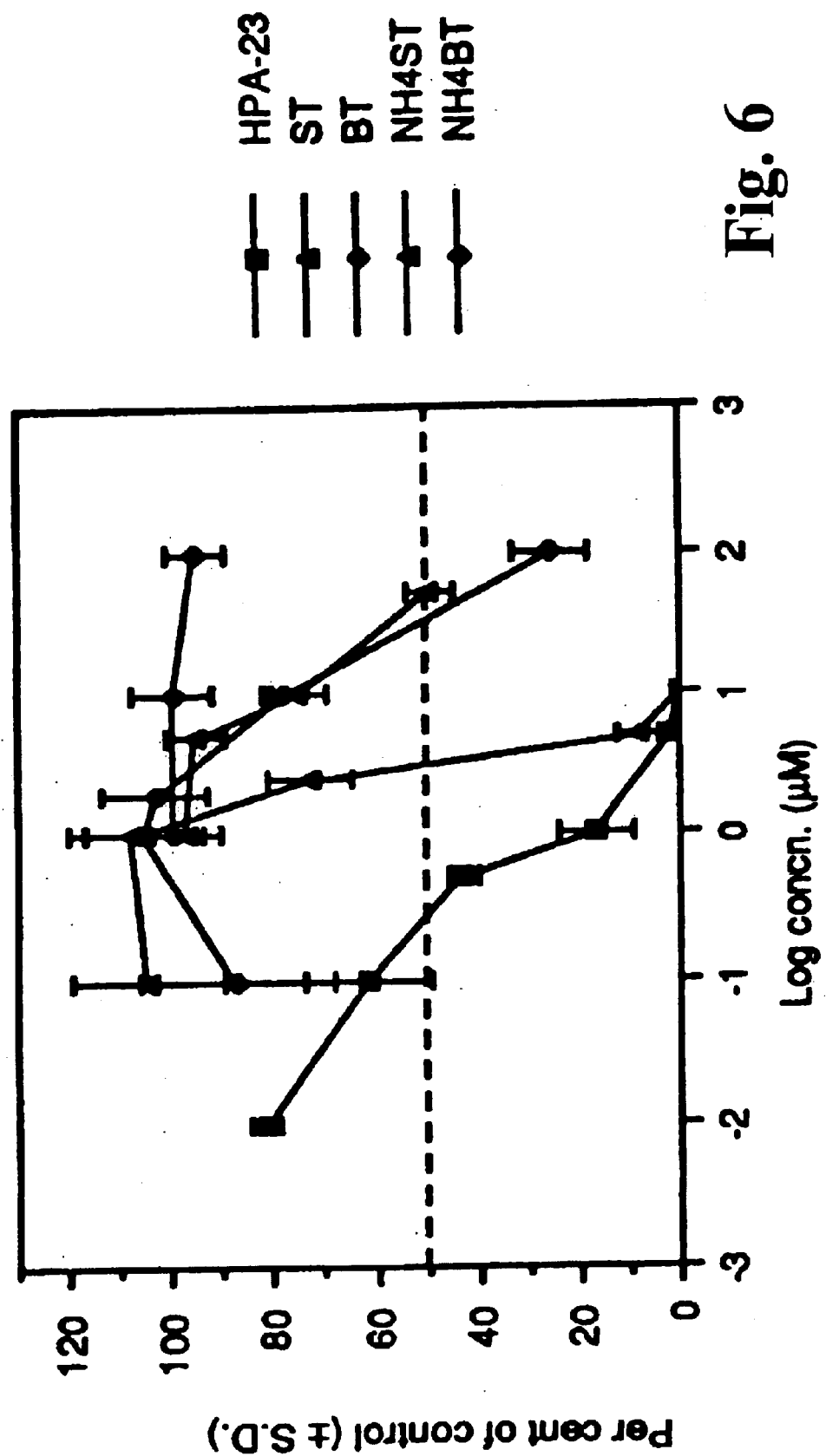
FIG. 6 shows the relative effect of various polyoxometalate compounds on colony formation of human granulocyte-macrophage precursor cells. The polyoxometalate compounds are.

The toxicities of a variety of polyoxometalates with respect to human bone marrow cells (human granulocyte-macrophage precursor cells) were assessed. The toxicities and trends in toxicity in these tests (results given below) were not the same as those displayed in mice toxicity studies. The bone marrow toxicity assays revealed some interesting and most encouraging results:

1) The ammonium salts proved to be substantially less toxic than the free acid forms of any given polyoxometalate, and
2) The following order of toxicity in these assays was established: ammonium BT=$NH_4BT$ (least toxic)<BT and $NH_4ST$<AZT and ST<HPA-23, the French polyoxometalate anti-HIV-1 agent currently in clinical trial (most toxic) (FIG. 6).

Ammonium BT displayed effectively no toxicity to these human bone marrow cells.

Replacing the inorganic cations of the polyoxometalates ($Na^+$, $K^+$, $H^+$, etc.) with ammonium and basic amino acid derived cations, does not adversely affect the otherwise high antiviral efficacy and low toxicity of the polyoxometalates shown in cell culture (PBMC), but the latter polyoxometalate salts show greatly improved toxicity to human bone marrow cells and markedly improved tolerance in mammals in general relative to the former salts.

Results of activity testing on some of the present compounds are shown in Table 2 below.

TABLE 2

RESULTS OF ACTIVITY TESTING ON POLYOXOMETALATE COMPOUNDS

| | | EC-50 (µM) | | | | | | | IC50 (µM) | |
|---|---|---|---|---|---|---|---|---|---|---|
| Compound Formula | Mol. Weight | Cell-Free RT (virion-derived) | HIV-1 (LAV-1) | HSV-1 | HSV-2 | Friend, Spleen (EY-10) | Mouse Ecotropic, CNS (CAS-Br-M) | SIV | Toxicity >100 µM = Nontoxic PBM Cells | Toxicity >100 µM = Nontoxic Vero Cells |
| AZT (Reference Compound) | 267 | $3.08 \times 10^{-3}$ | >100 | >100 | 0.01 | $7.3 \times 10^{-3}$ | $1.27 \times 10^{-3}$ $2.88 \times 10^{-3}$ | >100 | 29.0 µM |
| α $H_3PT$ | 2,988 (6 $H_2O$) | >100 | 13.98 | 12.7 | 18.7 | | | | | 10 µM |
| α and β $H_4ST$ | 3,004 (7 $H_2O$) | 26.1 | 0.12, 0.21 | 1.6 | 1.5 | 0.17 | | | | 80 µM |
| α and β $H_5BT$ | 3,042 (10 $H_2O$) | 2.6 | 0.46, 0.11, 0.44 | <1 | | 0.18 | | | 76%, 200 µM | 85 µM |

TABLE 2-continued

RESULTS OF ACTIVITY TESTING ON POLYOXOMETALATE COMPOUNDS

| | | EC-50 ($\mu$M) | | | | | | | IC50 ($\mu$M) | |
|---|---|---|---|---|---|---|---|---|---|---|
| Compound Formula | Mol. Weight | Cell-Free RT (virion-derived) | HIV-1 (LAV-1) | HSV-1 | HSV-2 | Friend, Spleen (EY-10) | Mouse Ecotropic, CNS (CAS-Br-M) | SIV | Toxicity >100 $\mu$M = Nontoxic PBM Cells | Toxicity >100 $\mu$M = Nontoxic Vero Cells |
| β H$_4$ST | 3,004 (7 H$_2$O) | 34.6 | 0.25 | 3.16 | 1.1 | 0.29 | | | >100 $\mu$M | 8 $\mu$M |
| H$_6$DT | 4,763 (15 H$_2$O) | 0.14 | 0.52 | 0.16 | 0.18 | | | | 90%, 100 $\mu$M | 81.9%, 100 $\mu$M |
| α (NH$_4$)$_6$DT | 4.865 (15 H$_2$O) | 0.13 | 0.91 | 0.33 | 0.24 | | | | 76%, 100 $\mu$M | 83%, 100 $\mu$M |
| α (NH$_4$)$_n$H$_{(4-n)}$ST | 3,111 (n = 1, 10 H$_2$O) | 17.3 | 2.4 (2.7, 2.26) | | | 0.18, 0.88 | 0.79 | 0.52 (0.042, 4.33, 1.01) | >100 $\mu$M | −50 $\mu$M |
| α (NH$_4$)$_n$H$_{(5-n)}$BT | 3,110 (n = 1, 10 H$_2$O) | 3.3 | 3.2 (3.17) | | | 0.49, 0.90 (0.70) | 1.16 | 2.3 (0.92, 1.42) | >100 $\mu$M | −50 $\mu$M |
| α-K$_5$BT | 3,233 (10 H$_2$O) | 2.9 | 0.36 | | | 0.19, 0.80 | 0.91 | | | −80 $\mu$M |
| (NH$_4$)$_5$BT | 2,947 | 68.1 | 6.69, 11.6 | >10 | >10 | | | | | >100 $\mu$M |
| Na$_5$BT | 2,972 | 32.2 | 3.61, 10.9 | >10 | >10 | | | | | >100 $\mu$M |
| (NH$_4$)$_4$W$_{10}$ | 2,423 | 24.2 | 2.00, 0.96 | >10 | 9.7 | 0.58 | | | >100 $\mu$M | >100 $\mu$M |
| (Me$_4$N)$_4$W$_{10}$ | 2,648 | 10.1 | 3.05, 3.30 | 5.98 | 8.78 | | | | | >100 $\mu$M |
| (HISH$^+$)$_n$H$^+_{(5-n)}$BT | 3,632 | 30.5 | 12 | >10 | >10 | | | | | >9.9 $\mu$M |
| (LYSH$^+$)$_n$H$^+_{(5-n)}$BT | 3,587 | 18.8 | 3.00, 4.3 | 6.69 | 2.78 | | | | >100 $\mu$M | >100 $\mu$M |
| (ARGH$^+$)$_n$H$^+_{(5-n)}$BT | 3,727 | 25.4 | 0.58, 1.70 | 1.35 | 3.16 | | | | 328 $\mu$M | >100 $\mu$M |
| (HISH$^+$)$_n$H$^+_{(4-n)}$ST | 3,194 | 22.3 | 0.22, 0.65 | 0.95 | 0.87 | 0.92 | | | 181.5 $\mu$M | >100 $\mu$M |
| (LYSH$^+$)$_n$H$^+_{(4-n)}$ST | 3,458 | 20.5 | 1.61, 0.68 | 0.32 | <1 | 0.95 | | | 2,447 $\mu$M | >100 $\mu$M |
| (ARGH$^+$)$_n$H$^+_{(4-n)}$ST | 3,570 | 14.2 | 1.03, 0.77 | 0.18 | <1 | 0.99 | | | >100 $\mu$M | >100 $\mu$M |
| HPA-23 (Reference Compound) | | | 0.29 | | | | | | | |

Assays in Infected Mice

Tests were conducted in whole infected mice using one of the compounds to the present invention. The methodology of this test is the same as was used in Ruprecht et al, Nature 323, 467–469, except that Friend virus was used instead of Rauscher virus. The results of these tests are shown in Table 3 below.

focus forming units (FFU)/mouse] was selected which caused a splenomegaly rate of 100% on day 16 after virus inoculation in untreated animals. The virus titer of the inoculum was determined by a UV/XC assay.

In vivo antiviral experiments. Mice were inoculated intraperitoneally with virus at noon and then randomized into ten animals per treatment group. Five hours after virus

TABLE 3

SPLENOMEGALY MODEL IN BALB/C MICE

| Treatment | Dose | Units | Administration | N | % Mortality | MDD | Mean Spleen wt. (mg) ± SD | % Effectiveness | Day of Sacrifice |
|---|---|---|---|---|---|---|---|---|---|
| PBS | 0 | mkd | IP QD × 10 | 10 | 0 | | 2,028 ± 508 | 0 | 16 |
| (ArgH$^+$)$_4$H$^+$BT | 10 | mkd | IP QD × 10 | 10 | 0 | | 2,287 ± 864 | −12.8 | 16 |
| (ArgH$^+$)$_4$H$^+$BT | 30 | mkd | IP QD × 10 | 10 | 0 | | 2,130 ± 693 | −5.0 | 16 |
| (ArgH$^+$)$_4$H$^+$BT | 60 | mkd | IP QD × 6 | 10 | 20 | 14.0 ± 0 | 644 ± 432 | 68.2 | 16 |
| AZT | 30 | mkd | IP QD × 10 | 10 | 0 | | 1,249 ± 1,152 | 38.4 | 16 |
| AZT | 60 | mkd | IP QD × 10 | 10 | 0 | | 988 ± 836 | 51.3 | 16 |

Abbreviations:
MDD: Mean day of death.
IP: Intraperitonally.
QD × 10: Once/day for 10 days.
QD × 6: Once/day for 6 days.
N: Number animals/jp.
PBS: Phosphate buffered saline.
mkd: mg/kg/d Comparison of Toxicity of Polyoxometalate Compounds Mice. Female BALB/c mice (3 to 4 weeks old), obtained from Charles River Laboratories (Raleigh, N.C.), were acclimatized in the animal facility for two weeks. They were then inoculated (200 $\mu$l) into the peritoneal cavity with Friend retrovirus, strain FV-PLS. A virus inoculum [about 100 inoculation, the mice were treated intraperitoneally with the compounds. Treatment was continued daily for 6 or 10 days. On day 16 after virus inoculation, the animals were sacrificed by carbon dioxide inhalation and their spleens removed under aseptic conditions and weighed. The results are shown in Table 4 below.

TABLE 4

COMPARISON OF TOXICITY OF POLYOXOMETALATE COMPOUNDS IN MICE
Drugs given BID × 6 - 60 mkd-given i.p.
Mice were bled on day 17

|  | PBS | alpha ST | NH4 ST | Arg ST | HPA-23 | Arg. HPA-23 | Alpha BT | NH4 BT | Arg BT |
|---|---|---|---|---|---|---|---|---|---|
| Mortality | 0/5 | 2/5 (40%) | 0/5 | 0/5 | 0/5 | 0/6 | 5/5 (100) | 5/5 (100) | 5/5 (100) |
| MDD ± St. Dev. | | 9.5 ± 3.5 | | | | | 3.8 ± 1.3 | 4.6 ± 0.89 | 8.8 ± 0.45 |
| WBC (×1000) | 8.5 ± 3.85 | 7.4 ± 3.96 | 7.18 ± 3.9 | 6.28 ± 2.19 | 4.16 ± 1.45 | 5.58 ± 1.55 | | | |
| RBC (×1000000) | 5.29 ± 2.5 | 4.59 ± 3.74 | 3.76 ± 1.57 | 3.95 ± 1.31 | 3.16 ± 0.95 | 3.74 ± 1.39 | | | |
| Hgb (g/dL) | 8.67 ± 4.3 | 8.25 ± 4.6 | 6.42 ± 2.39 | 7.08 ± 2.51 | 5.5 ± 1.43 | 7.72 ± 2.49 | | | |
| Hct (%) | 24.8 ± 11.54 | 21.35 ± 17.47 | 17.47 ± 7.08 | 18.16 ± 6.02 | 14.82 ± 4.44 | 17.42 ± 6.55 | | | |
| MCV (IL) | 46.63 ± 0.57 | 46.4 ± 0.28 | 43.38 ± 0.51 | 46.08 ± 0.45 | 46.86 ± 0.4 | 46.58 ± 0.33 | | | |
| MCH (pg) | 16.17 ± 0.67 | 20.85 ± 7 | 17.6 ± 4.64 | 17.8 ± 1.6 | 17.64 ± 2.07 | 21.38 ± 5.68 | | | |
| MCHC (g/dL) | 34.7 ± 1.74 | 44.95 ± 15.34 | 37.92 ± 9.82 | 38.62 ± 3.49 | 37.66 ± 4.32 | 45.9 ± 12.47 | | | |
| RDW (%) | 36.15 ± 3.04 | 35.6 ± 6.22 | 36.76 ± 2.63 | 36.68 ± 1.31 | 35.6 ± 2.12 | 36 ± 0.73 | | | |
| PLT (×1000) | 681.05 ± 147.15 | 247.35 ± 216.59 | 246.46 ± 43.58 | 325 ± 64.64 | 226.4 ± 165.94 | 448.02 ± 211.65 | | | |

MDD: Mean day of death
MCHC = mean corpuscular hemoglobin concentration
RDW = width of red cells
Hct = hematocrit
Hgb = hemaglobin
MCV = mean corpuscular volume
PLT = platelates Clearly, numerous modifications and variations of the present invention are possible in light of the above teachings. It is therefore understood that within the scope of the appended claims, the invention may be practiced otherwise than as specifically described herein.

What is claimed is:

1. A method of treating a retroviral infection in a mammal, comprising administering to a mammal in need thereof an effective amount of a compound having a formula selected from the group consisting of:

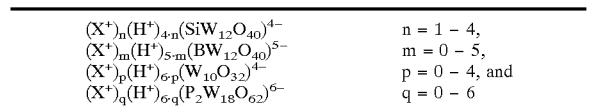

wherein X is selected from the group consisting of K, Na, $NH_4$, $(C_{1-5}\text{-alkyl})_4N$, protonated arginine, protonated lysine, and protonated histidine.

2. The method of claim 1, wherein said compound is

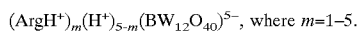

3. The method of claim 1, wherein said compound is

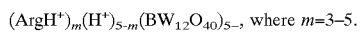

4. The method of claim 1, wherein said compound is

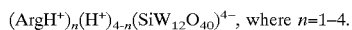

5. The method of claim 1, wherein said compound is administered orally or parenterally.

6. The method of claim 1, wherein said retrovirus is HIV-1 or HIV-2.

7. The method of claim 1, wherein said mammal is a human.

8. The method of claim 7, wherein said human is suffering from AIDS or ARC.

9. The method of claim 1, wherein said effective amount is 0.1 to 100 mg/kg total body weight/day.

10. A method of treating a retroviral infection in a mammal, which comprises administering to a mammal in need thereof an effective amount of a compound having a formula selected from the group consisting of:

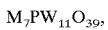

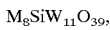

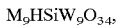

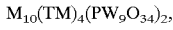

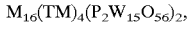

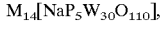

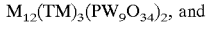, and

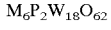

wherein M is an alkali metal ion, $NH_4^+$, histidinium ion, argininium ion, or lysinium ion, and
TM is a divalent transition metal ion.

11. The method of claim 10, wherein said divalent transition metal ion is selected from the group consisting of Mn, Fe, Co, Ni, Cu, and Zn.

12. The method of claim 10, wherein said compound is administered orally or parenterally.

13. The method of claim 10, wherein said retrovirus is HIV-1 or HIV-2.

14. The method of claim 10, wherein said mammal is a human.

15. The method of claim 14, wherein said human is suffering from AIDS or ARC.

16. The method of claim 10, wherein said effective amount is 0.1 to 100 mg/kg total body weight/day.

17. A composition for treating a retroviral infection in a mammal, which comprises:

(a) an effective amount of a compound having the molecular formula:

$(ArgH^+)_m(H^+)_{5-m}(BW_{12}O_{40})^{5-}$, where $m=1-5$; and (b) a pharmaceutically acceptable carrier.

18. A composition for treating a retroviral infection in a mammal, which comprises:

(a) an effective amount of a compound having the molecular formula:

$(ArgH^+)_m(H^+)_{5-m}(BW_{12}O_{40})^{5-}$, where $m=3-5$; and (b) a pharmaceutically acceptable carrier.

19. A composition for treating a retroviral infection in a mammal, which comprises:

(a) an effective amount of a compound having the molecular formula:

$(ArgH^+)_n(H^+)_{4-n}(SiW_{12}O_{40})^{4-}$, where $n=1-4$; and (b) a pharmaceutically acceptable carrier.

20. A composition for treating a retroviral infection in a mammal, which comprises:

(a) an effective amount of a compound having a molecular formula selected from the group consisting of:

$Na_9HSiW_9O_{34}$, $Na_8HPW_9O_{34}$, $K_{10}Cu_4(H_2O)_2(PW_9O_{34})_2$, $K_{10}Co_4(H_2O)_2(PW_9O_{34})_2$, and $(NH_4)_{14}(NaP_5W_{30}O_{110})$; and (b) a pharmaceutically acceptable carrier, wherein said composition is administered orally or parenterally.

* * * * *